United States Patent
Sugiura

(10) Patent No.: US 9,993,801 B2
(45) Date of Patent: Jun. 12, 2018

(54) ALDEHYDE-GAS-ADSORBING LIQUID AND GAS-ADSORBING PROCESSED PRODUCT USING SAME

(71) Applicant: TOAGOSEI CO., LTD., Tokyo (JP)

(72) Inventor: Koji Sugiura, Nagoya (JP)

(73) Assignee: TOAGOSEI CO., LTD., Tokyo (JP)

(*) Notice: Subject to any disclaimer, the term of this patent is extended or adjusted under 35 U.S.C. 154(b) by 99 days.

(21) Appl. No.: 15/106,936

(22) PCT Filed: Dec. 18, 2014

(86) PCT No.: PCT/JP2014/083541
§ 371 (c)(1),
(2) Date: Jun. 21, 2016

(87) PCT Pub. No.: WO2015/098687
PCT Pub. Date: Jul. 2, 2015

(65) Prior Publication Data
US 2017/0036187 A1  Feb. 9, 2017

(30) Foreign Application Priority Data

Dec. 24, 2013 (JP) ................... 2013-264883

(51) Int. Cl.
| | | |
|---|---|---|
| *B01J 20/22* | (2006.01) | |
| *A61L 9/012* | (2006.01) | |
| *A61L 9/01* | (2006.01) | |
| *B01J 20/06* | (2006.01) | |
| *B01J 20/08* | (2006.01) | |
| *B01J 20/10* | (2006.01) | |
| *B01J 20/32* | (2006.01) | |

(52) U.S. Cl.
CPC ............. *B01J 20/22* (2013.01); *A61L 9/01* (2013.01); *A61L 9/012* (2013.01); *B01J 20/06* (2013.01); *B01J 20/08* (2013.01); *B01J 20/103* (2013.01); *B01J 20/3231* (2013.01)

(58) Field of Classification Search
CPC ...... B01J 20/22; B01J 20/3231; B01J 20/103; B01J 20/08; B01J 20/06; A61L 9/00; A61L 9/01; A61L 9/012
See application file for complete search history.

(56) References Cited

U.S. PATENT DOCUMENTS

| | | |
|---|---|---|
| 2008/0187738 A1 | 8/2008 | Tonomura et al. |
| 2010/0297053 A1 | 11/2010 | Hirukawa |

FOREIGN PATENT DOCUMENTS

| | | |
|---|---|---|
| CN | 1432608 A | 7/2003 |
| JP | 10-226962 A | 8/1998 |
| JP | 2004-290543 A | 10/2004 |
| JP | 2005-253500 A | 9/2005 |
| JP | 2007-167495 A | 7/2007 |
| JP | 2007-215818 A | 8/2007 |
| JP | 2008-178788 A | 8/2008 |
| JP | 2008-190179 A | 8/2008 |
| JP | 2010-173343 A | 8/2010 |
| JP | 2011-1679 A | 1/2011 |
| WO | WO 2004/058311 A1 | 7/2004 |
| WO | WO 207/088879 A1 | 8/2007 |

OTHER PUBLICATIONS

International Search Report, issued in PCT/JP2014/083541, dated Mar. 31, 2015.
Written Opinion of the International Searching Authority, issued in PCT/JP2014/083541, dated Mar. 31, 2015.
Office Action dated May 4, 2017, in Chinese Patent Application No. 201480069662.2, with English translation.

*Primary Examiner* — Anthony J Zimmer
(74) *Attorney, Agent, or Firm* — Birch, Stewart, Kolasch & Birch, LLP

(57) ABSTRACT

To provide a transparent aldehyde-gas-adsorbing liquid that has high adsorption performance for an aldehyde gas and excellent processability and storage stability. To also provide an aldehyde-gas-adsorbing processed product such as a paper or a nonwoven fabric or fiber exhibiting excellent adsorption performance using the gas-adsorbing liquid.

An aldehyde-gas-adsorbing liquid that contains a dihydrazide compound and a metal oxide sol, the content of the dihydrazide compound being 1.3 to 6 mass % relative to the total amount of gas-adsorbing liquid, and the total content of the dihydrazide compound and the metal oxide sol solids content being 18 to 45 mass % relative to the total amount of gas-adsorbing liquid.

8 Claims, No Drawings

ALDEHYDE-GAS-ADSORBING LIQUID AND GAS-ADSORBING PROCESSED PRODUCT USING SAME

CROSS-REFERENCE TO RELATED APPLICATION

The disclosure of Japanese Patent Application No. 2013-264883, filed Dec. 24, 2013, is incorporated herein by reference in its entirety.

All publications, patent applications, and technical standards mentioned in this specification are herein incorporated by reference to the same extent as if each individual publication, patent application, or technical standard was specifically and individually indicated to be incorporated by reference.

TECHNICAL FIELD

The present invention relates to an aldehyde-gas-adsorbing liquid and an aldehyde-gas-adsorbing processed product using same.

BACKGROUND ART

In recent years, as seen in the sick house or sick building syndrome, health problems due to formaldehyde, etc. have been attracting attention. As a method for removing an aldehyde gas in an indoor environment, aldehyde gas adsorbents comprising an amine compound are known to be effective, and among them a dihydrazide compound is often used due to its large adsorption capacity and excellent safety, processability, etc. Furthermore, a technique for improving adsorptivity by supporting a dihydrazide compound on an inorganic compound is also known and has been disclosed in Patent Documents 1 to 4, etc.

Furthermore, Patent Document 5 discloses, as a material employing a gas-absorbing agent, a vehicle interior material comprising a substrate and a gas adsorbent attached to the substrate wherein the gas-absorbing agent is obtained by supporting an amino group- and/or imino group-containing organosilicon compound on a microparticulate support and neutralizing some or all of the amino groups and/or imino groups with at least one type of acid selected from the group consisting of carbonic acid, formic acid, and acetic acid.

Moreover, Patent Document 6 discloses, as a chemical for removing an aldehyde, a dispersion comprising 0.01 to 100 parts by weight of an aminoguanidine compound relative to 100 parts by weight of silica in an acidic silica sol.

Patent Documents 7 and 8 disclose a deodorant composition for an aldehyde, comprising a hydrazide compound such as adipic acid dihydrazide and a silica sol as active ingredients. Patent Document 7 discloses a composition comprising 10 to 1000 parts by mass of silica solids that can be mixed with 100 parts by mass of a hydrazide compound and having a total solids content mass of no greater than 5%. Furthermore, Patent Document 8 describes a composition comprising adipic acid dihydrazide and a silica sol at 1:2 as a comparative example.

PRIOR ART DOCUMENTS

Patent Documents

Patent Document 1 JP-A-2007-215818 (JP-A denotes a Japanese unexamined patent application publication)
Patent Document 2 JP-A-10-226962
Patent Document 3 International Patent Publication Laid-open No. 2004/058311
Patent Document 4 JP-A-2008-178788
Patent Document 5 JP-A-2010-173343
Patent Document 6 International Patent Publication Laid-open No. 2007/088879
Patent Document 7 JP-A-2004-290543
Patent Document 8 JP-A-2007-167495

SUMMARY OF THE INVENTION

Problems to be Solved by the Invention

In order to process a powdered adsorbent as disclosed in Patent Documents 1 to 4 into a paper, a nonwoven fabric, a fiber cloth, etc., it is necessary to prepare a suspension in which the powdered adsorbent is dispersed uniformly in an appropriately selected aqueous binder, coat a fiber cloth, etc. with this suspension, and then dry it by heating. However, it is not easy to disperse a powdered adsorbent in a binder as a uniform and stable suspension, aggregation might occur so that it becomes nonuniform, precipitation might occur over time, and it is difficult to obtain a dispersion that is stable for a long period of time. Because of this, it is impossible to form a uniform coating with a powdered adsorbent. Furthermore, in order to coat a fiber cloth, etc., it is easiest to carry out spraying, but if control of particle size of the powdered adsorbent is insufficient, a spray nozzle might be blocked, and depending on the degree of viscosity or aggregation of the suspension, spraying is often impossible. Other than spraying, immersion or coating requires special coating and drying equipment, and there are many industrial restrictions. Furthermore, since a powdered adsorbent makes a coated surface white after coating, it is impossible to use it for a dark-colored product or a product that requires a design. Moreover, since these chemical adsorbents exhibit adsorptivity by contact with a gas, a sufficient surface area is required, but due to the use of a binder an adsorbent powder is buried in a binder resin, and there is the problem that degradation of adsorption performance cannot be avoided.

Furthermore, a liquid absorbent disclosed in Patent Document 5 has good suitability for spraying but has the problem that the aldehyde gas adsorption performance is poor and the storage stability is low. Adipic acid dihydrazide is described as a comparative example, but it has problems with gas adsorption, hue, etc. A silica sol described in the above literature is a support that can replace a powdered inorganic compound to thus lead to an improvement in the adsorption performance; the appearance is that of a transparent liquid, and since a binder is not necessary for adhesion, the degree of technical improvement is larger than that of a powdered adsorbent.

Moreover, since the aminoguanidine compound of Patent Document 6 is a hydrochloride or a sulfate, the acidity is too strong, and there are the problems that corrosion occurs in a metal with which it is in contact at the time of processing or use, the binder is degraded, and a fiber, etc. on which it is spread is therefore discolored, etc.

The deodorant compositions described in Patent Documents 7 and 8 have a low total solids content, and in order to exhibit a practically sufficient ability to adsorb an aldehyde gas it is necessary to use an adsorbing liquid containing a large amount of water. Because of this, drying is not easy, depending on the weight per unit area of a substrate to be processed coating is impossible in one step due to an excess amount of water, and coating and drying steps need to be repeated a plurality of times. Furthermore, most of the adipic acid dihydrazide does not form a composite with the silica sol but remains dissolved in water, and there is the problem that the deodorizing performance after coating deteriorates since the adipic acid dihydrazide simply lies on the substrate on its own.

The end uses of these aldehyde gas deodorants include fiber products such as clothing or bedding for body odor of the elderly due to nonenal, etc., car mats or car seats for automobiles as a measure against VOC, interior products for tobacco, various filters, etc.; these are products that people are often in contact with in daily life, and consideration should be given to appearance and safety. Furthermore, it is best industrially to use an aldehyde-gas-adsorbing liquid, which does not require large-scale equipment for spray coating, for processing these end use fiber products, etc., and needless to say a colorless liquid adsorbent that can give gas adsorption performance with a smaller amount is better not only for processability but also in terms of transport and storage. However, an aldehyde-gas-adsorbing liquid that has a processability such that it can be used immediately as a liquid without requiring a binder, that has excellent storage stability, that is transparent and has no problems in terms of appearance, and that also has high aldehyde-gas-adsorption is not yet known.

The present invention has been accomplished in light of the above problems, and it is an object thereof to provide a transparent aldehyde-gas-adsorbing liquid that has high aldehyde gas adsorption performance and excellent processability and storage stability. It is also an object thereof to provide an aldehyde-gas-adsorbing processed product such as a fiber, a sheet, or a molded article that has been processed by spraying using the gas-adsorbing liquid and that exhibits excellent gas adsorption performance.

Means for Solving the Problems

The present inventors have found that an aldehyde-gas-adsorbing liquid having high aldehyde-gas-adsorbing properties and excellent processability and storage stability is obtained by mixing a dihydrazide compound and a metal oxide sol at a specific ratio.

That is, the present invention is as follows.
1. An aldehyde-gas-adsorbing liquid, comprising:
   a dihydrazide compound and a metal oxide sol,
   a content of the dihydrazide compound being from 1.3 mass % to 6 mass % relative to a total amount of the gas-adsorbing liquid, and
   a total content of the dihydrazide compound and a solid content of the metal oxide sol being from 18 mass % to 45 mass % relative to the total amount of the gas-adsorbing liquid.
2. The aldehyde-gas-adsorbing liquid according to 1, wherein a content of the solid content of the metal oxide sol in the aldehyde-gas-adsorbing liquid is at least six times larger than the content of the dihydrazide compound.
3. The aldehyde-gas-adsorbing liquid according to 1 or 2, wherein, after storage at 50° C. for one month, the gas-adsorbing liquid has an absorbance at a wavelength of 660 nm of 0.005 to 0.1 and a viscosity of no greater than 50 mPa·s.
4. The aldehyde-gas-adsorbing liquid according to any one of 1 to 3, wherein a substrate coated with the aldehyde-gas-adsorbing liquid does not whiten after drying.

5. An aldehyde-gas-adsorbing processed product formed by spray coating treatment using the aldehyde-gas-adsorbing liquid according to any one of 1 to 4.

Effects of the Invention

Since the aldehyde-gas-adsorbing liquid in the present invention comprises a dihydrazide compound and a metal oxide sol at a specific ratio, the aldehyde gas adsorption performance is high, and the processability and storage stability are excellent.

Specifically, since the aldehyde-gas-adsorbing liquid of the present invention has high adsorption performance for an aldehyde gas, merely coating various types of products of a room interior or a vehicle interior therewith enables an aldehyde gas in air to be reduced and emission of an aldehyde gas from the product to be suppressed. Furthermore, it is not necessary to add a resin binder, etc. when processing, and it becomes attached to a substrate simply by spray coating using a spray, etc. Since the substrate does not whiten after drying, it can be applied to a dark-colored substrate without impairing the appearance.

Moreover, the aldehyde-gas-adsorbing liquid of the present invention can be stored for over one month without forming a precipitate or a gel or causing discoloration as long as the temperature is within the range of 10° C. to 60° C.

MODE FOR CARRYING OUT THE INVENTION

One embodiment of the present invention is explained below, but the present invention should not be construed as being limited thereto. In addition, % denotes mass % and parts denotes parts by mass unless otherwise specified.

Furthermore, a numerical range denoted by 'to' means a numerical range that includes the values before and after the 'to'. Furthermore, in the present invention, 'mass %' has the same meaning as that of 'wt %', and 'parts by mass' has the same meaning as that of 'parts by weight'.

[1] Aldehyde-Gas-Adsorbing Liquid

The aldehyde-gas-adsorbing liquid related to the present invention comprises a dihydrazide compound and a metal oxide sol, the content of the dihydrazide compound being from 1.3 to 6 mass % relative to the total amount of gas-adsorbing liquid, and the total content of the dihydrazide compound and the solids content of the metal oxide sol being from 18 to 45 mass % relative to the total amount of gas-adsorbing liquid. The constituent components of the present invention are specifically explained.

The dihydrazide compound used in the present invention is a dihydrazide compound having two hydrazide groups per molecule and is represented by Formula 1 below.

$$H_2NHN-X-NHNH_2 \qquad (1)$$

[In the Formula, X denotes a —CO— group or a —CO-A-CO— group. A denotes an alkylene group or an arylene group.]

Examples of the alkylene group denoted by A in Formula 1 above include 1 to 12 carbon straight-chain alkylene groups such as a methylene group, an ethylene group, a trimethylene group, a tetramethylene group, a pentamethylene group, a hexamethylene group, a heptamethylene group, an octamethylene group, a nonamethylene group, a decamethylene group, and an undecamethylene group. The alkylene group may have a substituent, and examples of the substituent include a hydroxy group. Examples of the arylene group include a phenylene group, a biphenylene group, a naphthylene group, an anthrylene group, and a phenanthrylene group. Substituents for the arylene group include an alkyl group, a hydroxy group, and a halogen atom.

Specific examples of dihydrazide compounds of the formula (1) above include dibasic acid dihydrazides, such as carbodihydrazide (which is also called carbonic dihydrazide), oxalic dihydrazide, malonic dihydrazide, succinic dihydrazide, glutaric dihydrazide, adipic dihydrazide, azelaic dihydrazide, sebacic dihydrazide, 2-dodecanedioic dihydrazide, maleic dihydrazide, fumaric dihydrazide, diglycolic dihydrazide, tartaric dihydrazide, malic dihydrazide, isophthalic dihydrazide, terephthalic dihydrazide, dimer acid dihydrazide, and 2,6-naphthoic dihydrazide.

Among them, a dihydrazide compound having a small molecular weight is preferable. The reason therefor is that the smaller the molecular weight, the larger the gas adsorption capacity when the mass of the dihydrazide compound used is the same. It is also important that it is water-soluble and industrially available at low cost. A preferred dihydrazide compound is at least one selected from the group consisting of carbodihydrazide, succinic acid dihydrazide, adipic acid dihydrazide, and isophthalic acid dihydrazide. Adipic acid dihydrazide is more preferable since it is excellent in terms of storage stability of an aldehyde-gas-adsorbing liquid.

In addition, hydrazine is often used as a starting material for a dihydrazide compound, but since hydrazine is a compound that is strongly positive for mutagenicity, due to residual starting material the dihydrazide compound can become positive for mutagenicity. Because of this, it is preferable in the present invention to use a dihydrazide compound having a very small or zero hydrazine content, and adipic acid dihydrazide is preferable from this viewpoint.

The dihydrazide compound content is from 1.3 to 6 mass % relative to the total amount of aldehyde-gas-adsorbing liquid. This content is preferably from 1.4 to 5.5 mass %, and more preferably from 1.5 to 5 mass %. When the content is less than 1.3 mass %, since the aldehyde gas adsorption performance is poor, the coat weight necessary increases. As a result, spray coating sometimes cannot be completed in one step or it sometimes takes time to dry. On the other hand, when the content exceeds 6 mass %, there is a tendency for the storage stability of a gas-adsorbing liquid to be degraded and the dried gas-adsorbing processed product to whiten.

The metal oxide sol used in the present invention means a sol containing a metal or semimetal oxide and is a colloidal dispersion system in which water or a water-soluble solvent is used as a dispersion medium and silicon dioxide, aluminum oxide, etc. having a particle size of in the order of a few nm to a few hundred nm is used as a dispersoid. Commercially available metal oxide sols include a sodium-stabilized aqueous sol, an ammonia-stabilized sol, and an acidic aqueous sol. There are also alcoholic sols such as a methanol sol, but from the viewpoint of ease of handling an aqueous sol is preferable. The pH of the metal oxide sol is preferably neutral since there is no corrosivity and the storage stability is excellent. The solids content concentration of commercially available metal oxide sols is 10% to 50%, preferably at least 20% from the viewpoint of aldehyde-gas-adsorbing properties and processability, and preferably no greater than 40% when processability and storage stability are taken into consideration.

There is no restriction on the particle size of the metal oxide sol used in the present invention, but the larger the particles, the weaker the aggregation and the easier it is to disperse, whereas the finer it is the easier it is for it to be absorbed into various products such as fiber products and the more resistant it is to coming off after processing, which is preferable. Specifically, the median diameter measured by a laser diffraction type particle size distribution analyzer is preferably 5 to 100 nm, and more preferably 10 to 30 nm.

There is no restriction on specific components of the metal oxide sol used in the present invention, and examples include silicon dioxide, aluminum oxide, magnesium oxide, titanium oxide, and zirconium oxide. Among them, a silicon dioxide sol (silica sol) is preferable since it has excellent storage stability in particular.

Examples of commercially available aqueous silica sols include Snowtex O (product name, Nissan Chemical Industries Ltd.), Snowtex C (product name, Nissan Chemical Industries Ltd.), Snowtex OS (product name, Nissan Chemical Industries Ltd.), Snowtex OXS (product name, Nissan Chemical Industries Ltd.), Nalco 1034A (product name, Nalco Chemical Company), Nyacol 2034DI (product name, Eka Chemicals Aktiebolag), Cataloid SN (product name, JGC C & C), and Adelite AT-20Q (product name, ADEKA).

The total content of the dihydrazide compound and the solids content of the metal oxide sol in the present invention is from 18 to 45 mass % relative to the total amount of gas-adsorbing liquid, preferably from 19 to 43 mass %, and more preferably from 20 to 42 mass %. When the content is less than 18 mass %, it is necessary to spray a large amount of aldehyde-gas-adsorbing liquid, and spreading on a substrate may not be completed by one coating or it might take a long time for drying, which is not economical. On the other hand, when the content exceeds 45 mass %, the solids content concentration becomes too high, the storage stability becomes poor, the viscosity becomes high, and coating cannot be carried out in a stable manner.

With regard to the solids content of the metal oxide sol in the aldehyde-gas-adsorbing liquid, the solids content of the metal oxide sol is preferably at least 6 times the content of the dihydrazide compound, and more preferably at least 8 times but no greater than 15 times. The larger the amount of dihydrazide compound the larger the gas adsorption capacity tends to be, but the ratio of these two values has an appropriate value, and when it is at least 6 times, high gas adsorption can be achieved and the storage stability of the gas-adsorbing liquid improves. Furthermore, the larger the amount of dihydrazide compound the more cloudy a substrate coated with an aldehyde-gas-adsorbing liquid tends to be, thus impairing the appearance of a gas-adsorbing processed product. When the solids content of the metal oxide sol is no greater than 15 times the content of the dihydrazide compound, even if a sufficient amount for aldehyde-gas-adsorption to be exhibited is coated, the problem with whitening can be suppressed.

With regard to a process for producing the aldehyde-gas-adsorbing liquid of the present invention, production is possible by dissolving a dihydrazide compound in a metal oxide sol. It may be produced by stirring at a dissolution temperature of 10° C. to 50° C. for a dissolution time of about 1 hour. The higher the dissolution temperature, the faster it can dissolve, but when it is too high gelling easily occurs and there is a possibility of reprecipitation of the dihydrazide compound when the temperature is lowered, and it is preferable to carry out dissolution at 15° C. to 30° C. Since it is dissolved in a short period of time, stirring does not require special equipment, and a general-purpose mixer can be used. Furthermore, a storage container for the aldehyde-gas-adsorbing liquid of the present invention is preferably a plastic container or a glass container since a metallic container might be corroded to thus affect the product quality due to contamination with foreign matter, coloration, etc.

The aldehyde-gas-adsorbing liquid of the present invention preferably does not become a gel after long term storage and maintains transparency. Specifically, the absorbance at a wavelength of 660 nm when stored at 50° C. for one month is preferably 0.005 to 0.1. When in this range, a product coated with the gas-adsorbing liquid does not whiten. Furthermore, the viscosity after being stored at 50° C. for one month is preferably no greater than 50 mPa·s. When the viscosity is within this range, it is possible to combine the liquid with another additive such as a solvent or a dispersant as necessary.

The increase in viscosity of the adsorbing liquid after being stored at 50° C. for one month with respect to the viscosity of the adsorbing liquid before storage (initial viscosity) is preferably no greater than 10%.

In the present invention, the viscosity of the adsorbing liquid may be measured using a model B viscometer at 25° C.

It is possible to add a small amount of a polyol or an organic solvent such as ethanol to the aldehyde-gas-adsorbing liquid used in the present invention, thus improving the storage stability, the processability, etc., but an aqueous dispersion using a metal oxide sol liquid on its own is preferable.

The aldehyde-gas-adsorbing liquid of the present invention has high adsorption performance with an aldehyde gas. Examples of aldehyde gases include acetaldehyde, formaldehyde, propanal, butanal, and nonenal. The aldehyde-gas-adsorbing liquid of the present invention and an aldehyde-gas-adsorbing liquid other than the aldehyde-gas-adsorbing liquid of the present invention may be used in combination. Examples of the other aldehyde-gas-adsorbing liquid include ammonium sulfate, polyallylamine hydrochloride, EDTA sodium salt, triethanolamine, pyridine, dimethylhydantoin, casein, urea, thiourea, sodium casein, glycine, hexamethylenetetramine, guanidine nitrate, and hydroxylamine sulfate.

With respect to the method of using the aldehyde-gas-adsorbing liquid of the present invention, the aldehyde-gas-adsorbing liquid is used only for aldehyde gas as an object, and the aldehyde-gas-adsorbing liquid can be mixed with a deodorant for gas other than aldehyde gas (deodorant composition), or can be used in combination with such another deodorant. As a specific example which is mixed with or used in combination with the aldehyde-gas-adsorbing liquid of the present invention, there can be mentioned a basic gas deodorant for deodorizing basic gas, such as ammonia or trimethylamine. As examples of the basic gas deodorants, there can be mentioned tetravalent metal phosphate compounds insoluble in or unlikely to be soluble in water. Specific preferred examples of the tetravalent metal phosphate compounds include zirconium phosphate, titanium phosphate, and tin phosphate. In these compounds, there are those which are crystalline and have various crystal systems, such as an α form crystal, a β form crystal, a γ form crystal, and a NASICON form crystal, and those which are amorphous, and any of the compounds having a gas adsorbing property can be mixed with or used in combination with the aldehyde-gas-adsorbing liquid of the present invention.

Further, the aldehyde-gas-adsorbing liquid of the present invention can be mixed with or used in combination with a sulfur gas deodorant for deodorizing sulfur gas, such as hydrogen sulfide or methylmercaptan. For example, the aldehyde-gas-adsorbing liquid of the present invention can be mixed with or used in combination with a tetravalent metal phosphate compound having supported thereon ions of at least one metal selected from copper, zinc, and manganese, zinc oxide, copper silicate or zinc silicate. Among the metal ions to be supported on the tetravalent metal phosphate compound, especially preferred are copper ions because high deodorizing effect for hydrogen sulfide or the like is obtained.

For supporting metal ions on the tetravalent metal phosphate compound, the tetravalent metal phosphate compound may be contacted with a solution of a salt of metal ions to support the ions by ion-exchange or the like.

The amount of the metal ions supported can be controlled arbitrarily within the ion-exchange capacity for a tetravalent metal phosphate compound up to 100% if desired.

Further, with respect to zinc oxide, copper silicate, and zinc silicate, preferred is one having a large specific surface area because it has high deodorizing performance.

Further, the aldehyde-gas-adsorbing liquid of the present invention can be mixed with or used in combination with an organic acid gas deodorant for deodorizing malodorous gas, such as acetic acid, isovaleric acid, or butyric acid. For example, a deodorant composition can be obtained by mixing hydrated zirconium oxide, hydrated titanium oxide, silica gel, zeolite and activated carbon with the aldehyde-gas-adsorbing liquid of the present invention.

[2] Aldehyde-Gas-Adsorbing Processed Product

In order to obtain the aldehyde-gas-adsorbing processed product of the present invention, the surface of a paper, a nonwoven fabric, a fiber cloth, etc. may be spray-coated with the aldehyde-gas-adsorbing liquid or it may be immersed in the aldehyde-gas-adsorbing liquid. Since drying in a subsequent step is easy, spray coating is preferable. After the aldehyde-gas-adsorbing liquid is sprayed, moisture is transpired by air drying, hot air drying, etc. to thus fix the adsorbent. This drying may be achieved by natural drying or heating at room temperature to about 200° C. Furthermore, in order to strengthen fixation to a substrate such as a fiber, a known binder resin such as an acrylic acid-based resin or a urethane-based resin may be used in a combination with the aldehyde-gas-adsorbing liquid of the present invention.

The spray-coat weight of the aldehyde-gas-adsorbing liquid of the present invention is preferably 3 to 200 $g/m^2$, and more preferably 5 to 150 $g/m^2$.

When the spray-coat weight is at least 3 $g/m^2$, sufficient aldehyde gas adsorption performance can be exhibited, and when it is no greater than 200 $g/m^2$, fixation and whitening are suppressed.

EXAMPLES

The present invention is more specifically explained below, but should not be construed as being limited thereby. In the description below, parts and % are on a mass basis.

1. Evaluation Methods (1) Storage Stability

A gas-adsorbing liquid was placed in a 100 mL polyethylene container and stored in a temperature controlled oven at 50° C. for one month, and the absorbance, appearance, and viscosity after storage were measured. The absorbance was measured at a wavelength of 660 nm using an absorption spectrometer for a gas-adsorbing liquid placed in a 1 cm wide glass cell. The appearance was examined by eye. The viscosity was measured at 25° C. using a model B viscometer, and stability was evaluated using the increase in viscosity with respect to the viscosity of the adsorbing liquid before storage (initial viscosity). When the absorbance is no greater than 0.1, it can be said that the gas-adsorbing liquid is transparent.

(2) Gas Adsorption Capacity of Gas-Adsorbing Liquid 0.02 g of a powder obtained by drying the gas-adsorbing liquid at 120° C. was placed in a 5 L vinyl fluoride bag (a vinyl fluoride film was used by forming it into a bag shape, called a 'Tedlar bag' below), 3 L of air containing acetaldehyde gas at 600 ppm was injected thereinto, and the bag was allowed to stand at room temperature (15° C. to 25° C.) for 2 hours. Subsequently, the concentration of acetaldehyde gas remaining in the Tedlar bag was measured using a gas detector (Gastec Corporation, the same product being used below), and the adsorption capacity was calculated by subtracting the amount reduced in a blank test measured using an empty Tedlar bag from the amount of gas reduced per g of the gas adsorbent (solids content) (units mL/g, mL denotes the volume of gas in the standard state).

(3) Appearance and Adsorptivity of Gas-Adsorbing Processed Product

One surface of a black fabric (10 cm×10 cm) was spray-coated with the gas-adsorbing liquid (10 g/m$^2$) using a hand spray and air-dried for one day, thus producing a gas-adsorbing processed product. The appearance of this gas-adsorbing processed product was examined by eye, and the appearance after coating was evaluated. Subsequently, this gas-adsorbing processed product was placed in the Tedlar bag, 3 L of air containing acetaldehyde gas at 14 ppm was injected thereinto, and the bag was allowed to stand at room temperature (15° C. to 25° C.) for 2 hours. Subsequently, the concentration of acetaldehyde gas remaining in the Tedlar bag was measured using a gas detector. The percentage reduction relative to a fabric that had not been sprayed with the gas-adsorbing liquid was defined as the gas adsorptivity (adsorptivity, %).

2. Production and Evaluation of Aldehyde-Gas-Adsorbing Liquid

Examples 1 to 5

An aldehyde-gas-adsorbing liquid was produced by combining adipic acid dihydrazide, a silica sol, and water so as to give a solids content shown in Table 1 and stirring them at room temperature for 1 hour.

With regard to this liquid, the storage stability, the adsorption capacity of the gas-adsorbing liquid, and the appearance and adsorptivity of a gas-adsorbing processed product were evaluated and are shown in Table 2. The abbreviations in Table 1 mean the materials below.

Amine a1: adipic acid dihydrazide, reagent grade, Tokyo Chemical Industry Co., Ltd.
Amine a2: succinic acid dihydrazide, Japan Finechem Inc.
Amine a3: aminoguanidine sulfate, reagent grade, Wako Pure Chemical Industries, Ltd.
Amine a4: γ-(2-aminoethyl)aminopropyltrimethoxysilane, Dow Corning
Silica sol b1: product name 'Snowtex C30', median diameter; 10 to 25 nm, pH; 8.5 to 9.0, solids content concentration; 31 mass %, Nissan Chemical Industries Ltd.
Silica sol b2: product name 'Snowtex C40', median diameter; 10 to 25 nm, pH; 8.5 to 9.0, solids content concentration; 40 mass %, Nissan Chemical Industries Ltd.
Alumina sol: product name 'Alumina Sol 520', median diameter; 16 µm, pH 4.1, solids content concentration; 20 mass %, Nissan Chemical Industries Ltd.
Silica gel: product name 'Sylysia 350', median diameter; 4 µm, Fuji Silysia Chemical Ltd.

Example 6

An aldehyde-gas-adsorbing liquid was produced by carrying out the same procedure as in Example 1 except that silica sol b2 was used instead of silica sol b1. With regard to this liquid, the storage stability, the adsorption capacity of the gas-adsorbing liquid, and the appearance and adsorptivity of the gas-adsorbing processed product were evaluated.

Example 7

An aldehyde-gas-adsorbing liquid was produced by carrying out the same procedure as in Example 1 except that alumina sol was used instead of silica sol b1. With regard to this liquid, the storage stability, the adsorption capacity of the gas-adsorbing liquid, and the appearance and adsorptivity of the gas-adsorbing processed product were evaluated.

Example 8

An aldehyde-gas-adsorbing liquid was produced by carrying out the same procedure as in Example 1 except that succinic acid dihydrazide was used instead of adipic acid dihydrazide. With regard to this liquid, the storage stability, the adsorption capacity of the gas-adsorbing liquid, and the appearance and adsorptivity of the gas-adsorbing processed product were evaluated.

Comparative Examples 1 to 6

An aldehyde-gas-adsorbing liquid was produced by combining adipic acid dihydrazide, a silica sol, and water so as to give a solids content shown in Table 1 and stirring them at room temperature for 1 hour. With regard to this liquid, the storage stability, the adsorption capacity of the gas-adsorbing liquid, and the appearance and adsorptivity of the gas-adsorbing processed product were evaluated and are shown in Table 2.

Comparative Example 7

An aldehyde-gas-adsorbing liquid was produced by carrying out the same procedure as in Example 1 except that silica sol b2 was used instead of silica sol b1. With regard to this liquid, the storage stability, the adsorption capacity of the gas-adsorbing liquid, and the appearance and adsorptivity of the gas-adsorbing processed product were evaluated.

Comparative Example 8

An aldehyde-gas-adsorbing liquid was produced by carrying out the same procedure as in Example 1 except that aminoguanidine sulfate was used instead of adipic acid dihydrazide. With regard to this liquid, the storage stability, the adsorption capacity of the gas-adsorbing liquid, and the appearance and adsorptivity of the gas-adsorbing processed product were evaluated.

Comparative Example 9

An aldehyde-gas-adsorbing liquid was produced by carrying out the same procedure as in Example 1 except that succinic acid dihydrazide was used instead of adipic acid dihydrazide. With regard to this liquid, the storage stability, the adsorption capacity of the gas-adsorbing liquid, and the appearance and adsorptivity of the gas-adsorbing processed product were evaluated.

Comparative Example 10

An aldehyde-gas-adsorbing liquid was produced by carrying out the same procedure as in Example 1 except that amine a4 was used instead of adipic acid dihydrazide. With regard to this liquid, the storage stability, the adsorption capacity of the gas-adsorbing liquid, and the appearance and adsorptivity of the gas-adsorbing processed product were evaluated.

Comparative Example 11

An aldehyde-gas-adsorbing liquid was produced by carrying out the same procedure as in Example 1 except that a silica gel was used instead of silica sol b1. With regard to this liquid, the storage stability, the adsorption capacity of the gas-adsorbing liquid, and the appearance and adsorptivity of the gas-adsorbing processed product were evaluated.

Comparative Example 12

An aldehyde-gas-adsorbing liquid was produced by carrying out the same procedure as in Example 1 except that a silica sol was not used and an acrylic emulsion was used for processing the fabric. With regard to this liquid, the storage stability, the adsorption capacity of the gas-adsorbing liquid, and the appearance and adsorptivity of the gas-adsorbing processed product were evaluated.

TABLE 1

|  | Amine type | Amine content (mass %) | Metal oxide sol type | the solids content of Metal oxide sol (mass %) | Total content (mass %) | Metal oxide sol/amine mass ratio |
|---|---|---|---|---|---|---|
| Example 1 | a1 | 3 | Silica sol b1 | 18 | 21 | 6.0 |
| Example 2 | a1 | 3 | Silica sol b1 | 20 | 23 | 6.7 |
| Example 3 | a1 | 3 | Silica sol b1 | 30 | 33 | 10.0 |
| Example 4 | a1 | 5 | Silica sol b1 | 30 | 35 | 6.0 |
| Example 5 | a1 | 1.5 | Silica sol b1 | 20 | 21.5 | 13.3 |
| Example 6 | a1 | 3 | Silica sol b2 | 38 | 41 | 12.7 |
| Example 7 | a1 | 3 | Alumina sol | 20 | 23 | 6.7 |
| Example 8 | a2 | 3 | Silica sol b1 | 20 | 23 | 6.7 |
| Comparative Example 1 | a1 | 7 | Silica sol b1 | 30 | 37 | 4.3 |
| Comparative Example 2 | a1 | 5 | Silica sol b1 | 10 | 15 | 2.0 |
| Comparative Example 3 | a1 | 3 | Silica sol b1 | 3 | 6 | 1.0 |
| Comparative Example 4 | a1 | 3 | Silica sol b1 | 10 | 13 | 3.3 |
| Comparative Example 5 | a1 | 3 | Silica sol b1 | 13 | 16 | 4.3 |
| Comparative Example 6 | a1 | 1 | Silica sol b1 | 15 | 16 | 15.0 |
| Comparative Example 7 | a1 | 1 | Silica sol b2 | 38 | 39 | 38.0 |
| Comparative Example 8 | a2 | 7 | Silica sol b1 | 30 | 37 | 4.3 |
| Comparative Example 9 | a3 | 3 | Silica sol b1 | 20 | 23 | 6.7 |
| Comparative Example 10 | a4 | 3 | Silica sol b1 | 20 | 23 | 6.7 |
| Comparative Example 11 | a1 | 3 | Silica gel | 20 | 23 | 6.7 |
| Comparative Example 12 | a1 | 5 | None | 0 | 5 | 0 |

TABLE 2

|  | Absorbance | Liquid appearance | Increase in viscosity (%) | Adsorption capacity (ml/g) | Appearance after coating | Adsorptivity (%) |
|---|---|---|---|---|---|---|
| Example 1 | 0.01 | No change | <10 | 11 | No change | 90 |
| Example 2 | 0.02 | No change | <10 | 12 | No change | 93 |
| Example 3 | 0.02 | No change | <10 | 15 | No change | 98 |
| Example 4 | 0.02 | No change | <10 | 20 | No change | 95 |
| Example 5 | 0.02 | No change | <10 | 9 | No change | 92 |
| Example 6 | 0.03 | No change | <10 | 18 | No change | 99 |
| Example 7 | 0.03 | No change | <10 | 11 | No change | 89 |
| Example 8 | 0.09 | No change | <10 | 9 | No change | 86 |
| Comparative Example 1 | 0.15 | Precipitate | <10 | 12 | Whitening | 88 |

TABLE 2-continued

|  | Absorbance | Liquid appearance | Increase in viscosity (%) | Adsorption capacity (ml/g) | Appearance after coating | Adsorptivity (%) |
|---|---|---|---|---|---|---|
| Comparative Example 2 | 0.02 | No change | <10 | 10 | Very slight whitening | 82 |
| Comparative Example 3 | 0.02 | No change | <10 | 5 | No change | 78 |
| Comparative Example 4 | 0.02 | No change | <10 | 6 | No change | 80 |
| Comparative Example 5 | 0.02 | No change | <10 | 7 | No change | 81 |
| Comparative Example 6 | 0.01 | No change | <10 | 6 | No change | 57 |
| Comparative Example 7 | 0.03 | No change | <10 | 7 | No change | 67 |
| Comparative Example 8 | 0.34 | Gelled | Measurement not possible | 10 | Whitening | 88 |
| Comparative Example 9 | 0.71 | Gelled | Measurement not possible | 15 | No change | 99 |
| Comparative Example 10 | 0.66 | Yellowed, gelled | Measurement not possible | 4 | No change | 64 |
| Comparative Example 11 | — | No change | 220 | 12 | Whitening | 59 |
| Comparative Example 12 | 0.01 | No change | <10 | 3 | No change | 37 |

In the Examples, there was no change in the appearance of the liquids after storage at 50° C. for one month, and the transparency was maintained. Furthermore, the viscosity hardly changed from the initial viscosity (1 to 20 mPa·s), showing excellent storage stability. Moreover, the gas-adsorbing liquids of the Examples had a large adsorption capacity per g of solids content and gave a processed product having high gas adsorptivity.

On the other hand, in the Comparative Examples, the absorbance decreased and gelling occurred after storage at 50° C. for one month, and it was confirmed that the storage stability was poor. Furthermore, the gas adsorption performance tended to be poor.

INDUSTRIAL APPLICABILITY

The aldehyde-gas-adsorbing liquid in the present invention has excellent aldehyde gas adsorption performance, processability, and storage stability. Furthermore, a processed product produced using this aldehyde-gas-adsorbing liquid does not have an impaired appearance. It is therefore possible, by applying it to various interior or car interior products where an aldehyde gas should be suppressed, to easily reduce the concentration of an aldehyde gas in the environment.

What is claimed is:

1. An aldehyde-gas-adsorbing liquid, comprising:
a dihydrazide compound and a metal oxide sol, wherein:
a content of the dihydrazide compound being from 1.3 mass % to 6 mass % relative to a total amount of the gas-adsorbing liquid,
a total content of the dihydrazide compound and a solid content of the metal oxide sol being from 18 mass % to 45 mass % relative to the total amount of the gas-adsorbing liquid, and
a content of the solid content of the metal oxide sol in the aldehyde-gas-adsorbing liquid is at least six times larger than the content of the dihydrazide compound.

2. The aldehyde-gas-adsorbing liquid according to claim 1, wherein, after storage at 50° C. for one month, the gas-adsorbing liquid has an absorbance at a wavelength of 660 nm of 0.005 to 0.1 and a viscosity of no greater than 50 mPa·s.

3. The aldehyde-gas-adsorbing liquid according to claim 1, wherein a substrate coated with the aldehyde-gas-adsorbing liquid does not whiten after drying.

4. An aldehyde-gas-adsorbing processed product formed by spray coating treatment using the aldehyde-gas-adsorbing liquid according to claim 1.

5. The aldehyde-gas-adsorbing processed product according to claim 4, wherein a spray-coat weight of the aldehyde-gas-adsorbing liquid is 3 to 200 g/m².

6. The aldehyde-gas-adsorbing liquid according to claim 1, wherein the dihydrazide compound is at least one selected from the group consisting of carbodihydrazide, succinic acid dihydrazide, adipic acid dihydrazide, and isophthalic acid dihydrazide.

7. The aldehyde-gas-adsorbing liquid according to claim 1, wherein the metal oxide sol is at least one selected from the group consisting of silicon dioxide, aluminum oxide, magnesium oxide, titanium oxide, and zirconium oxide.

8. The aldehyde-gas-adsorbing liquid according to claim 1, wherein the content of the solid content of the metal oxide sol in the aldehyde-gas-adsorbing liquid is at least 8 times but no greater than 15 times than the content of the dihydrazide compound.

* * * * *